(12) United States Patent
Glasnapp

(10) Patent No.: US 9,415,054 B2
(45) Date of Patent: Aug. 16, 2016

(54) PIROXICAM TRANSDERMAL COMPOSITION TO TREAT PLANTAR FASCIITIS

(71) Applicant: Professional Compounding Centers of America (PCCA), Houston, TX (US)

(72) Inventor: Andrew B. Glasnapp, Sugar Land, TX (US)

(73) Assignee: Professional Compounding Centers of America (PCCA), Houston, TX (US)

( * ) Notice: Subject to any disclaimer, the term of this patent is extended or adjusted under 35 U.S.C. 154(b) by 504 days.

(21) Appl. No.: 13/917,304

(22) Filed: Jun. 13, 2013

(65) Prior Publication Data

US 2014/0371211 A1  Dec. 18, 2014

(51) Int. Cl.
| | |
|---|---|
| *A61K 31/54* | (2006.01) |
| *A61K 31/5415* | (2006.01) |
| *A61K 9/00* | (2006.01) |
| *A61K 47/24* | (2006.01) |
| *A61K 9/06* | (2006.01) |

(52) U.S. Cl.
CPC ............ *A61K 31/5415* (2013.01); *A61K 9/0014* (2013.01); *A61K 9/06* (2013.01); *A61K 47/24* (2013.01)

(58) Field of Classification Search
CPC ...................................................... A61K 31/54
USPC ....................................................... 514/222.2
See application file for complete search history.

(56) References Cited

U.S. PATENT DOCUMENTS

| 5,227,165 A | 7/1993 | Domb et al. |
|---|---|---|
| 5,505,960 A | 4/1996 | Assogna |
| 2008/0004284 A1 | 1/2008 | Hart et al. |
| 2012/0277195 A1 | 11/2012 | Banov et al. |
| 2013/0085171 A1 | 4/2013 | Ray et al. |
| 2014/0371211 A1 | 12/2014 | Glasnapp |

FOREIGN PATENT DOCUMENTS

| WO | WO 2012109151 A1 | 8/2012 |
|---|---|---|
| WO | PCT/US2014/041848 | 2/2015 |

OTHER PUBLICATIONS

Meltzer, "Effective Protocol for the Management of Plantar Fasciitis", May 31, 2011, Publisher: Practical Pain Management (http://www.practicalpainmanagement.com) first published on May 31, 2011, pp. 1-7.
PCCA, "Commonly Requested Pain Management Compounds", 2009, p. 1, II. 8-9.

*Primary Examiner* — Raymond Henley, III
(74) *Attorney, Agent, or Firm* — David G. Woodral; Fellers, Snider, Blankenship, Bailey & Tippens, P.C.

(57) ABSTRACT

A transdermal composition and method to be used as a treatment for plantar fasciitis is provided. Transdermal composition may include a combination of about 2% w/w to about 5% w/w of piroxicam and about 95% w/w to about 98% w/w of a natural permeation enhancement (NPE) composition. The NPE composition may increase the skin permeability, enhancing the transdermal delivery flux of piroxicam via a single transdermal application, thus, reducing the time of treatment. Transdermal composition may be applied upon an area of treatment, which may include myofascial trigger points linked to pain caused by plantar fasciitis, thus treating this condition more effectively. Moreover, employing a long acting NSAID such as piroxicam, in combination with the NPE composition, may act as a faster and effective treatment for an inflammatory process compared to typical treatments.

19 Claims, 2 Drawing Sheets

PIROXICAM TRANSDERMAL COMPOSITION TO TREAT PLANTAR FASCIITIS

CROSS-REFERENCE TO RELATED APPLICATIONS

N/A

BACKGROUND

1. Field of the Disclosure

The present disclosure relates in general to pharmaceutical compositions, and more specifically to a transdermal composition and methods to treat plantar fasciitis.

2. Background Information

Plantar fasciitis is a painful inflammatory process of the plantar fascia, the connective tissue on the sole (bottom surface) of the foot. It may be often caused by overuse of the plantar fascia or arch tendon of the foot. Plantar fasciitis may be a very common condition and may be difficult to treat if not looked after properly. An incidental finding associated with this condition may be a heel spur, a small bony calcification on the calcaneus heel bone, in which case it is the underlying plantar fasciitis that may produce the pain, and not the spur itself. The condition is responsible for the creation of the spur; the plantar fasciitis is not caused by the spur.

Typical treatments for plantar fasciitis may include indications to get rest and avoid the use of the foot in pain, the use of orthotics or boots, administering of low doses of drugs directed to treatment of the symptoms experienced by the individual patient, such as oral anti-inflammatories or injections of corticosteroids; and invasive surgery, among other treatments. These types of treatments may involve applying the drug, therapy, or surgery where the pain is located; nevertheless, the percentage of effectiveness of a surgery is from about 30% to about 60%. Additionally, there may be a high number of cases of plantar fasciitis that may be misdiagnosed and may be actually myofascial trigger points, or may be using a treatment that may not be as effective as it is needed.

Local anesthetics may block the generation and conduction of nerve impulses by increasing the threshold for electrical excitation in the appropriate nerve, by slowing the propagation of the nerve impulse, and by reducing the rate of rise of the action potential. Local anesthetics may be extremely potent and may result in a virtually complete loss of sensation in the treated area of the body.

Pharmaceutical analgesics may include a variety of classes of drugs, such as general anesthetics, non-steroidal anti-inflammatories, and local anesthetics. General anesthetics may reduce pain by producing a loss of consciousness. Local anesthetics may cause a loss of sensation in a localized area of the body without a loss of consciousness. Non-steroidal anti-inflammatories (NSAIDs) may ameliorate the pain but do not cause a loss of sensation or consciousness.

The NSAIDs such as piroxicam is generally administered orally, once or twice daily. NSAIDs may be less potent than the centrally acting narcotics and may have a different spectrum of side effects. The major adverse reactions of oral NSAIDs may include gastrointestinal tract ulceration, bleeding and perforation, blurred and/or diminished vision, edema, and prolonged bleeding time.

Accordingly, there is still a need for a composition and method to transdermally alleviate pain for an extended period of time, without the need for frequent administration of a drug, having a faster and more effective action to alleviate the pain caused by this inflammatory process.

SUMMARY

The present disclosure may include a composition that may alleviate pain caused by plantar fasciitis. The composition may be employed as a transdermal formulation. A method for preparing such transdermal formulation is also described here.

In an embodiment, a transdermal composition is provided. Pain caused by plantar fasciitis may be alleviated by applying a pharmaceutically effective amount of the transdermal composition. The transdermal composition may include a combination of about 2% w/w of piroxicam with about 95% w/w to about 98% w/w of a natural permeation enhancement (NPE) composition. The NPE composition may enable an effective administration of the piroxicam, thus improving treatment outcomes.

In one embodiment, the NPE composition may include one or more phospholipids, one or more oils having essential fatty acids, behenic acid, and oleic acid, one or more skin lipids, and a butter having linoleic acid and linolenic acid.

In another embodiment, the NPE composition may include a combination of about 0.05% w/w to about 5% w/w of one or more phospholipids, about 1% w/w to about 20% w/w of one or more oils having essential fatty acids, such as behenic acid, and oleic acid, where one of the one or more oils may be pracaxi oil, about 0.1% w/w to about 3% w/w of one or more skin lipids, and about 1% w/w to about 10% w/w of a butter having linoleic acid and linolenic acid.

In other embodiments, the NPE composition may include a combination of a hydrogenated phospholipid, an unsaturated phospholipid, pracaxi oil; *Plukenetia volubilis* seed oil, ceramide, squalene, and *Vitellaria paradoxa* (formerly known as *Butyrospermum parkii*) butter.

In further embodiments, the NPE composition may include a combination of about 10% w/w to about 50% w/w of pracaxi oil, about 15% w/w to about 40% w/w of patauá oil, about 10% w/w to about 30% w/w of inaja oil, and about 10% w/w to about 30% w/w of one or more suitable emollients. Furthermore, other suitable compositions may include a combination of about 1% w/w to about 20% w/w of pracaxi oil, about 10% w/w to about 40% w/w of one or more phospholipids, about 5% w/w to about 20% w/w of one or more of patauá oil (seje oil) or inaja oil, and about 5% w/w to about 30% w/w of one or more emulsifiers.

According to various embodiments, the transdermal composition may be applied to myofascial trigger points associated with pain in the foot's bottom surface, such as the pain caused by plantar fasciitis. Transdermal composition may be administrated in a dose of about 0.5 g to about 2 g, once a day for about 7 days to about 60 days.

Numerous other aspects, features and benefits of the present disclosure may be made apparent from the following detailed description.

BRIEF DESCRIPTION OF THE DRAWINGS

The present disclosure can be better understood by referring to the following figures. The components in the figures are not necessarily to scale, emphasis instead being placed upon illustrating the principles of the disclosure. In the figures, reference numerals designate corresponding parts throughout the different views.

DETAILED DESCRIPTION

Figure 1:
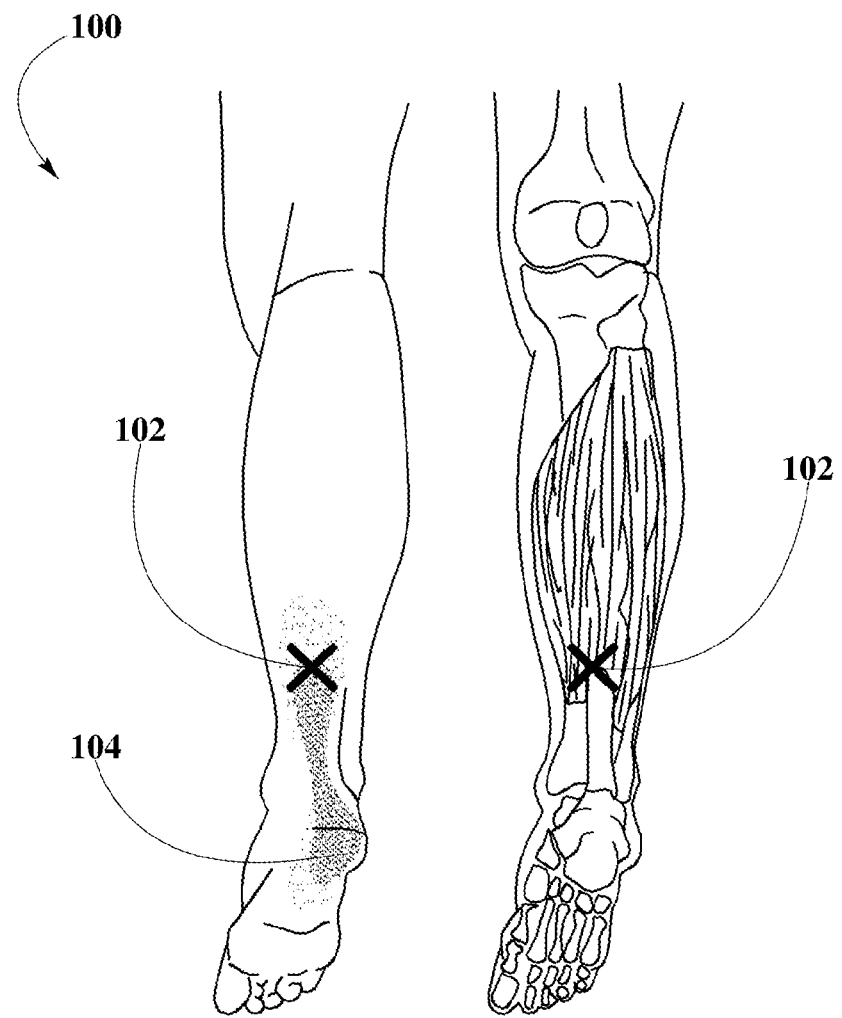
FIG. 1 illustrates an area of treatment showing a myofascial trigger point of a heel pain, where transdermal composition may be applied, according to an embodiment.

The present disclosure is here described in detail with reference to embodiments illustrated in the drawings, which form a part here. Other embodiments may be used and/or other changes may be made without departing from the spirit or scope of the present disclosure. The illustrative embodiments described in the detailed description are not meant to be limiting of the subject matter presented here.

DEFINITIONS

As used here, the following terms may have the following definitions:

"Gel" refers to a colloid in which the solid disperse phase forms a network in combination with that of the fluid continuous phase, resulting in a viscous semirigid sol.

"Lysophospholipids" (LPL) refers to any phospholipid that is missing one of its two O-acyl chains.

"Liposomes" refers to artificially prepared vesicles made of lipid bilayer, and having concentric phospholipid bilayers.

"Giant liposomes" refers to liposomes whose size may range from about 10,000 to about 100,000 nm.

"LUV liposomes" refers to liposomes that are larger than about 50 nm.

"Multilamellar liposomes" (MLV) refers to liposomes that range from about 500 to about 10,000 nm in size.

"SUV liposomes" refers to liposomes that are smaller than about 50 nm.

"Unilamellar liposomes" refers to small unilamellar vesicle (SUV) liposomes or large unilamellar vesicle (LUV) liposomes.

"Oil" refers to a vegetable substance which may be clear, odorless, viscous, hydrophobic, liquid or liquefiable at room temperature. Oils may be widely used in cosmetics due to its hypoallergenic and noncomedogenic properties.

"Permeation enhancement" refers to an increase in the permeability of the skin or mucosal tissue to the selected active pharmaceutical ingredient.

"Phospholipids" refers to fat-like organic compounds that resemble triglycerides, but have a fatty acid with a phosphate-containing polar group.

"Silicone" refers to polymeric organic silicone compounds obtained as oils.

"Skin lipids" refers to those lipids that are present at the skin's surface.

"Solution" refers to a pharmaceutical preparation consisting of a semisolid emulsion of either the oil-in-water or the water-in-oil type, ordinarily intended for topical or transdermal use.

"Treating" and "Treatment" refer to reduction in severity and/or frequency of symptoms, elimination of symptoms and/or underlying cause, prevention of the occurrence of symptoms and/or their underlying cause, and improvement or remediation of damage.

DESCRIPTION OF THE DRAWINGS

The present disclosure may relate to a long-acting transdermal composition that may be indicated for the treatment of plantar fasciitis. The transdermal composition may include a combination of piroxicam and a natural permeation enhancement (NPE) composition, which may include one or more naturally occurring substances, including one or more oils rich in essential fatty acids.

Plantar fasciitis is a painful inflammatory process of the plantar fascia, the connective tissue on the sole (bottom surface) of the foot. Plantar fasciitis may often be caused by overuse of the plantar fascia or arch tendon of the foot, thus, plantar fasciitis may be a very common condition and may be difficult to treat if not looked after properly. An incidental finding associated with this condition may be a heel spur, a small bony calcification on the calcaneus heel bone, in which case it may be the underlying plantar fasciitis that produces the pain, and not the spur itself. The condition is responsible for the creation of the spur; the plantar fasciitis is not caused by the spur.

Typical treatments or therapies may include the administration of a drug where the pain is located, or may even recommend an invasive surgery; however, the pain may be referred in a location elsewhere in the body, called trigger point. Trigger points, may also be known as trigger sites or muscle knots, and may be described as hyperirritable spots in skeletal muscle that may be associated with palpable nodules in taut bands of muscle fibers.

The trigger point model states that unexplained pain may frequently radiate from these points of local tenderness to broader areas, sometimes distant from the trigger point itself. Practitioners claim to have identified reliable referred pain patterns which may associate pain in one location with trigger points elsewhere.

Compression of a trigger point may elicit local tenderness, referred pain, or local twitch response. Trigger points form only in muscles and may form as a local contraction in a small number of muscle fibers in a larger muscle or muscle bundle, which in turn may pull on tendons and ligaments associated with the muscle and may cause pain deep within a joint where there are no muscles.

Referred pain from trigger points may mimic the symptoms of a very long list of common maladies, but physicians, in weighing all the possible causes for a given condition, rarely consider a myofascial source, which may lead to false diagnoses and the ultimate failure to deal effectively with pain.

Myofascial trigger points may be hypersensitive areas which keep a portion of the muscle or surrounding soft tissues contracted. The term "myofascial" is the combination of two Latin words, 'myo' which means muscle and 'fascia' for connective tissue in and around the muscle. An active myofascial trigger point may be a localized area that is starving for oxygen, resulting in release of neuroreactive biochemicals which sensitize nearby nerves. The sensitized nerves may then initiate the motor, sensory, and autonomic effects of myofascial trigger points by acting on the central nervous system. Myofascial trigger points may be identified and documented electrophysiologically and may also be identified histologically by contraction knots. Trigger points may cause pain, tingling, burning, weakness, and restricted motion.

In most mammalian bodies, there is a myofascial trigger point in the calf that may refer pain to the bottom of the foot, such as pain caused by plantar fasciitis; therefore, by treating such myofascial trigger point, pain caused by plantar fasciitis at the bottom of the foot may be alleviated. Using a transdermal composition with enhanced permeation effects and a non-steroidal anti-inflammatory drug (NSAID) such as piroxicam, which is a long acting drug, into the myofascial trigger point of plantar fasciitis, may effectively alleviate intense pain caused by this inflammatory process.

Transdermal Composition

Piroxicam

Piroxicam is a cyclooxygenase inhibiting NSAID of the oxicam class generally used to relieve the symptoms of rheumatoid and osteoarthritis, primary dysmenorrhoea, and postoperative pain, and may act as an analgesic, especially where there is an inflammatory component. As an NSAID, piroxicam may be a non-selective Cox inhibitor possessing both analgesic and antipyretic properties. Additionally, piroxicam may undergo enterohepatic circulation.

Piroxicam's long half-life may enable it to be administered once daily. The anti-inflammatory effect of Piroxicam may result from the reversible inhibition of cyclooxygenase, causing the peripheral inhibition of prostaglandin synthesis. The prostaglandins are produced by an enzyme called Cox-1. Piroxicam may block the Cox-1 enzyme, resulting into the disruption of production of prostaglandins. Piroxicam may also inhibit the migration of leukocytes into sites of inflammation and may prevent the formation of thromboxane A2, an aggregating agent, by the platelets. Piroxicam may also have a role as a major mediator of inflammation and/or a role for prostanoid signaling in activity-dependent plasticity.

Metabolism of Piroxicam may occur by hydroxylation at the 5 position of the pyridyl side chain and conjugation of this product; by cyclodehydration; and by a sequence of reactions involving hydrolysis of the amide linkage, decarboxylation, ring contraction, and N-demethylation. In vitro studies have indicated cytochrome P4502C9 (CYP2C9) as the main enzyme involved in the formation to the 5'-hydroxy-Piroxicam, the major metabolite.

Natural Permeation Enhancement (NPE) Composition

The NPE composition may be employed to enhance the effect of piroxicam. The NPE composition may include one or more naturally occurring substances, including one or more phospholipids, one or more oils rich in essential fatty acids, behenic acid, and oleic acid, one or more skin lipids, and one or more butters rich in linoleic acid and linolenic acid. According to an embodiment, NPE composition may be employed as a penetration enhancer for a number of different compounds, including topical cosmetics and pharmaceutical formulations. While the NPE composition may be safe and effective, this composition may include natural ingredients which may assist with penetration of an active pharmaceutical ingredient (API) through the skin. NPE composition having fatty acid micro-particles described here may include, among other components, behenic acid, oleic acid, omega-3 fatty acids, and phospholipids. The use of a permeation enhancing composition may eliminate the need for pre-encapsulation of the APIs.

As mentioned, the NPE composition described here may include one or more naturally occurring substances, including one or more phospholipids, one or more oils rich in essential fatty acids, behenic acid, and oleic acid, one or more skin lipids, and one or more butters rich in linoleic acid and linolenic acid. The ingredients within NPE composition act synergistically to increase the skin permeation of water and oil soluble products. The NPE composition, which is a solution, may be added to a gel or emulsion at a given percent to give permeation power to the otherwise transdermal preparation. When the NPE composition is prepared, liposomes may be formed from the fatty acids, including behenic acid and oleic acid that may be present in the one or more oils, and may be stabilized by the phospholipids in the composition. More specifically, when the NPE composition is added to water or a water-incorporating composition, liposomes may be formed.

Phospholipids

In some embodiments, liposomes may be filled with drugs or other APIs and may be used to deliver these drugs. Liposomes may include naturally-derived phospholipids with mixed lipid chains or other surfactants. In some embodiments, the liposomes that may be formed may be used to deliver drugs or other APIs transdermally to the skin's surface. The liposomes that may be formed using embodiments of the present disclosure may be stabilized by the phospholipids, in addition to their small and relatively uniform particle size. Various molecules from those having a low molecular weight, such as glucose, to those having a high molecular weight, such as peptides and proteins, may be incorporated in liposomes. Water soluble compounds/drugs may be present in aqueous compartments while lipid soluble compounds/drugs and amphiphilic compounds/drugs may insert themselves in phospholipid bilayers. The liposomes having drugs may be administered by various routes, including intravenous, oral inhalation, local application, and ocular, among others. Because of this, liposomes may be used for the treatment of many diseases. Liposomes may be either unilamellar or multilamellar.

Additionally, due to their amphiphilic character, liposomes may be a powerful solubilizing system for a wide range of compounds. In addition to these physico-chemical properties, liposomes may exhibit many special biological characteristics, including specific interactions with biological membranes and various cells. These properties point to several possible applications with liposomes as the solubilizers for difficult-to-dissolve substances, dispersants, sustained release systems, delivery systems for the encapsulated substances, stabilizers, protective agents, microencapsulation systems and micro reactors, among others. Liposomes may be made entirely from naturally occurring substances and may be, therefore, nontoxic, biodegradable, and non-immunogenic.

Oils

Another component present in the NPE composition described here may be oils that are rich sources of essential fatty acids, behenic acid, and oleic acid. The supply of essential fatty acids and antioxidant molecules may restore the cutaneous permeability and the function of the skin barrier. The supply of essential fatty acids and antioxidant molecules may also contribute to the control of the imperceptible water loss and maintain moisture of the skin.

Behenic acid and oleic acid, when used by themselves, may be irritating when applied to the skin, which makes behenic acid and oleic acid difficult to use as permeation enhancers. While having an irritating effect on the skin, these acids may also be effective vehicles at delivering APIs through the skin. In one embodiment, NPE composition may include pracaxi oil.

Pracaxi Oil

Pracaxi oil may be rich in organic acids with antioxidant, antibacterial, and antifungal properties. Pracaxi oil may be obtained from the seed oil of *Pentaclethara macroloba* tree. Pracaxi oil may include about 20% w/w behenic acid and about 35% w/w oleic acid. In some cases, pracaxi oil may include more than these percentages. As the behenic acid and oleic acid may be present in the oil, the effects of the acids may be less irritating on the skin, and as such makes the oil a good choice for one of the ingredients of a penetration enhancer. This oil has been widely employed for its cosmetic, therapeutic, and medicinal properties. Scientific studies have shown that pracaxi oil may have strong antibacterial, antiviral, antiseptic, antifungal, anti-parasitic, and anti-hemorrhagic properties.

The oil may have a high amount of solid matter, not fatty acids, which make it solidify in cooler temperatures. The solid matter has gentle moisturizers and high cellular renewal properties, includes Vitamin E and has essential fatty acids, which may make it a suitable oil for products intended to address sensitive skins.

The fatty acid composition of pracaxi oil is illustrated below in table 1.

TABLE 1

Fatty acid composition of pracaxi oil.

| Fatty Acidds | Carbon Atoms | Composition % |
|---|---|---|
| Lauric | 12:00 | 1.3000 |
| Myristic | 14:00 | 1.2100 |
| Palmitic | 16:00 | 2.0400 |
| Stearic | 18:00 | 2.1400 |
| Oleic | 18:10 | 44.3200 |
| Linoleic | 18:20 | 1.9600 |
| Linolenic | 18:30 | 2.3000 |
| Behenic | 22:00 | 19.6700 |
| Lignoceric | 24:00 | 14.8100 |

*Plukenetia volubilis* Seed Oil

Another oil that may be used in some embodiments in combination with pracaxi oil is *Plukenetia volubilis* seed oil, also known as Inca Inchi. *Plukenetia volubilis* seed oil is native to the Amazon Rainforest. The seeds of Inchi may be high in protein (around 27% w/w) and oil (around 35% w/w to around 60% w/w) content. *Plukenetia volubilis* seed oil extracted from the *Plukenetia volubilis* plant may be one of the largest plant sources of the Omega family of fatty acids, including a high concentration of protein. *Plukenetia volubilis* seed oil may also be rich in iodine and vitamin A and vitamin E. *Plukenetia volubilis* seed oil may be a natural oil with an exceptional content in polyunsaturated fatty acids (greater than 90% w/w) and tocopherols (1.5 to 2 g/kg). *Plukenetia volubilis* seed oil may be a unique vegetable oil having both essential fatty acids in such a high amount, including 49% w/w of alphalinolenic acid (omega-3) and 34% of linoleic acid (omega-6). While *Plukenetia volubilis* seed oil has a very high amount of fatty acids, it may also have high amounts of behenic acid (10% w/w to 30% w/w) and oleic acid (35% w/w to 80% w/w).

Inaja Oil

Still yet another oil that may be used is from a tree called *Maximiliana maripapaim*, or Inaja. Inaja tree is an indigenous Amazonian palm widespread in the state of Para, growing around the Amazon River estuary. Inaja tree may have one of the highest sources of lauric acid (greater than 40% w/w) and oleic acid (greater than 15% w/w). Further, the highest concentration of fatty acids found in the Inaja tree may be found in the kernal oil, as opposed to the pulp oil. Oil from Inaja tree is extracted from the fruits of the inaja palm, which may include of about 70% w/w short-chain fatty acids, including lauric acid and myristic acid. This palm has been used in the production of bar soap because of its high concentration of lauric acid. The fatty acid composition of inaja kernel oil is shown in table 3 below.

TABLE 3

Fatty acid composition of inaja kernel oil.

| Fatty Acids | Carbon Atoms | Composition % |
|---|---|---|
| Lauric | 12:00 | 40.5000 |
| Myristic | 14:00 | 25.0000 |
| Palmitic | 16:00 | 9.0000 |
| Stearic | 18:00 | 2.4000 |
| Oleic | 18:10 | 10.8000 |
| Linoleic | 18:20 | 1.9600 |
| Linolenic | 18:30 | 2.4000 |
| Behenic | 22:00 | trace |
| Lignoceric | 24:00 | trace |

As mentioned, behenic acid, lauric acid, oleic acid, and other fatty acids, when used by themselves, may be very rough on the skin. But, when an oil such as *Plukenetia volubilis* seed oil and/or pracaxi oil and/or inaja oil are used, they may work to enhance the restoration of cutaneous barrier organization and epidermal elasticity, in addition to contributing to the control of imperceptible water loss, thus maintaining skin hydration. This may be, at least in part, due to the high amounts of essential fatty acids in these oils. The link between skin permeation and hydration is clear. Increasing the permeability of the stratum corneum may be achieved by the increase of water content in this tissue. Hydration by occlusion may cause a swelling of the corneocytes and, subsequently, may increase the skin permeation of APIs. Here, the utilization of physiological lipids, essential fatty acids, and phospholipids, may provide penetration power with restorative benefits to the skin. While *Plukenetia volubilis* seed oil, pracaxi oil, and inaja oil have been mentioned here, other oils may also be used in alternative compositions, including patauá oil or seje oil.

Seje Oil

Seje or patauá oil is extracted from the mesocarp of the patauá palm and generally appears as a greenish-yellow and transparent liquid, with little odor and taste, having the physical appearance and composition of fatty acids that are similar to olive oil (*Olea europaea*). It may have high content of unsaturated fatty acids. Due to its high content of oleic acid, seje oil may be used as skin moisturizers. The dry mesocarp of patauá palm may include about 7.4% w/w protein and possess an excellent amino acid composition. Because of this, the protein of patauá may be one of the most valuable found among plants and may be compared with the meat or milk from cattle. The most abundant sterols may be $\Delta^5$avenosterol and β-sitosterol, with relative contents of about 35% w/w and about 38% w/w, respectively. The most abundant aliphatic alcohols may be those with 7, 8 and 10 carbon atoms. Among tocopherols, α-tocopherol may be predominant. Aldehydes, such as heptanal, octanal, and decanal may be present in the volatile fraction along with terpenoid compounds.

The fatty acid composition of seje oil is illustrated below in table 2.

TABLE 2

Fatty acid composition of seje oil.

| Fatty Acids | Carbon Atoms | Composition % |
|---|---|---|
| Palmitic | 16:00 | 13.2 |
| Polmitolcic | 16:10 | — |
| Stearic | 18:00 | 3.6 |
| Oleic | 18:10 | 77.7 |

TABLE 2-continued

Fatty acid composition of seje oil.

| Fatty Acids | Carbon Atoms | Composition % |
|---|---|---|
| Linoleic | 18:20 | 2.7 |
| Linolenic | 18:30 | 0.6 |
| Arachidic | 20:00 | 2 |
| Unsaturated | | 81.6 |

Skin Lipids

Another component of the NPE composition may be skin lipids. Examples of skin lipids that may be used in NPE composition may include ceramides and/or squalene. Ceramides are the major lipid constituent of lamellar sheets. Ceramides may be a structurally heterogeneous and complex group of sphingolipids including derivatives of sphingosine bases in amide linkage with a variety of fatty acids. Differences in chain length, type, and extent of hydroxylation and saturation may be responsible for the heterogeneity of the epidermal sphingolipids. Ceramides may play an important role in structuring and maintaining the water permeability barrier function of the skin. In conjunction with the other stratum corneum lipids, they may form ordered structures. A structured semi-occlusive barrier that increases skin hydration may be a positive influence on the penetration of API.

Another skin lipid that may be used is squalene, which is a lipid fat in the skin. When used together with a ceramide and a phospholipid, such as phosphatidylcholine, the formulation is mild such that it may be used on even sensitive skin. Squalene may also help to decrease water evaporation, thus speeding up skin permeation of actives and decreasing irritation made by surfactants found in emulsions. Squalene, being a natural emollient, may impart an elegant feel to formulations in which it is used. Squalene may be excellent for use in skin care and to help skin to retain moisture and feel soft and conditioned without feeling greasy.

Butters

Yet another component of NPE composition may be butters rich in linoleic acid and linolenic acid. One example of this type of butter may be *Butyrospermum parkii* butter, also known as shea butter. Other exemplary butters that may be used in embodiments of the present disclosure may include cupuacu butter, buriti butter, passionfruit butter, mango butter, tucuma butter, palm butter, murumu butter, chamomile butter, cocoa butter, orange butter, lemon grass butter, avocado butter, tamanu butter, aloe butter, shea butter, monoi butter, pomegranate butter, almond butter, jojoba butter, red palm butter, acai butter, olive butter, matcha green tea butter, brazil nut butter, macadamia butter, kokum butter, mafura butter, coffee butter, tucuma butter, ucuúba butter, bacuri butter, and chamomile butter.

In embodiments of the present disclosure, the use of behenic acid, oleic acid, phospholipids, and the omega family may enhance the permeation of drugs or other active ingredients through the skin in-vitro and in-vivo.

As mentioned, NPE composition may be produced such that the size of the particles may range between about 5 microns and about 20 microns, which may provide a more stable vesicle than if the particle sizes were larger. Various methods may be used to produce particle sizes of about 5 microns to about 20 microns. In one embodiment, a high pressure homogenizer may be used.

While concentrations of the components included in NPE composition described here may vary, table 4 below illustrates exemplary concentrations, including the four main components described above, a concentration range, and optimal concentrations for each of the four components.

TABLE 4

Exemplary concentrations of the components within NPE composition.

| Ingredients | Range Concentration | Optimal Concentration |
|---|---|---|
| Phospholipids | 0.05-5% | 2% |
| Oils | 1-20% | 3% |
| Skin Lipids | 0.1-3% | 0.5% |
| Butters | 1-10% | 2% |

In one embodiment, the formulation may include between about 5% w/w and about 0% w/w of Phosal 75 SA (alcohol; purified phosphatidylcholine; safflower oil; glyceryl stearate; coconut oil, ascorbyl palmitate); between about 5% w/w and about 40% w/w of DMS 3015 (water, alcohol, caprylic/capric triglyceride, hydrogenated lecithin, *Butyrospermum parkii* butter, squalene, and ceramide 3); between about 5% w/w and about 20% w/w of Inca Inchi (*Plukenetia volubilis* seed oil, tocopherol); between about 5% w/w and about 40% w/w of pracaxi oil; and between about 10% w/w and about 90% w/w of purified water.

In one embodiment, a natural composition to be used for skin permeation is provided. The NPE composition may include a combination of about 0.05% w/w to about 5% w/w of one or more phospholipids, about 1% w/w to about 20% w/w of one or more oils having essential fatty acids, such as behenic acid, and oleic acid, where one of the one or more oils may be pracaxi oil, about 0.1% w/w to about 3% w/w of one or more skin lipids, and about 1% w/w to about 10% w/w of a butter having linoleic acid and linolenic acid.

In another embodiment, a composition to be used for skin permeation is provided. The composition may include a combination of a hydrogenated phospholipid, an unsaturated phospholipid, pracaxi oil; *Plukenetia volubilis* seed oil, ceramide, squalene, and *Vitellaria paradoxa* (formerly known as *Butyrospermum parkii*) butter.

In other embodiments, the composition may include a combination of about 10% w/w to about 50% w/w of pracaxi oil, about 15% w/w to about 40% w/w of patauá oil, about 10% w/w to about 30% w/w of inaja oil, and about 10% w/w to about 30% w/w of one or more suitable emollients. Furthermore, other suitable composition may include a combination of about 1% w/w to about 20% w/w of pracaxi oil, about 10% w/w to about 40% w/w of one or more phospholipids, about 5% w/w to about 20% w/w of one or more of Patauá oil or Inaja oil, and about 5% w/w to about 30% w/w of one or more emulsifiers.

Manufacturing Method

A method for preparing a natural composition to be used as a transdermal formulation for the treatment of plantar fasciitis may include the combination of various components to form a transdermal composition. These components may include suitable concentrations of piroxicam, pracaxi oil, andiroba oil, copaíba balsam, and ucuúba butter. The transdermal composition may be dispersed in a vessel using a high shear homogenizer. The transdermal composition may be mixed in different batches and then all the batches may be mixed together. Mixing rates may vary, and may include speeds between about 1000 RPM and about 5000 RPM. Negative pressure may be created in the vessel having the transdermal composition. In one embodiment, the pressure may reach about negative 2.5 bars, although this pressure may vary. The negative pressure, in one embodiment, may be created by a vacuum system. The methods presented here may allow for the size of the liposomes to reach the range of about 5 microns to about 20 microns, which allows for more stable particles and better skin permeation than larger particle sizes.

Plantar Fasciitis Treatment Employing Piroxicam Transdermal Composition

In an embodiment, pain caused by plantar fasciitis may be alleviated by applying a pharmaceutically effective amount of the transdermal composition. The transdermal composition may include a combination of about 2% w/w to about 5% w/w of piroxicam with about 95% w/w to about 98% w/w of a NPE composition. NPE composition may enable an effective administration of piroxicam, thus improving treatment outcomes.

In an embodiment, the NPE composition may include one or more phospholipids, one or more oils having essential fatty acids, behenic acid, and oleic acid, one or more skin lipids, and a butter having linoleic acid and linolenic acid. One of the oils used in the NPE composition may be pracaxi oil.

In various embodiments, the NPE composition may include a combination of about 0.05% w/w to about 5% w/w of one or more phospholipids, about 1% w/w to about 20% w/w of one or more oils having essential fatty acids, such as behenic acid, and oleic acid, where one of the one or more oils may be pracaxi oil, about 0.1% w/w to about 3% w/w of one or more skin lipids, and about 1% w/w to about 10% w/w of a butter having linoleic acid and linolenic acid.

In another embodiment, the NPE composition may include a combination of a hydrogenated phospholipid, an unsaturated phospholipid, pracaxi oil; *Plukenetia volubilis* seed oil, ceramide, squalene, and *Vitellaria paradoxa* (formerly known as *Butyrospermum parkii*) butter.

In other embodiments, the NPE composition may include a combination of about 10% w/w to about 50% w/w of pracaxi oil, about 15% w/w to about 40% w/w of patauá oil (seje oil), about 10% w/w to about 30% w/w of inaja oil, and about 10% w/w to about 30% w/w of one or more suitable emollients. Furthermore, other suitable composition may include a combination of about 1% w/w to about 20% w/w of pracaxi oil, about 10% w/w to about 40% w/w of one or more phospholipids, about 5% w/w to about 20% w/w of one or more of patauá oil or inaja oil, and about 5% w/w to about 30% w/w of one or more emulsifiers.

The NPE composition may increase the skin permeability of APIs, passing the stratum corneum and reaching the target area, particularly, because of the oil's high concentrations of oleic, linolenic, linoleic acids, and sterols, particularly beta-sitosterol and stigmasterol. Ingredients within the NPE composition, act synergistically to increase the skin permeation of water and oil soluble products. When the NPE composition described here is prepared, liposomes may be formed from the fatty acids, including behenic acid and oleic acid that may present on one or more oils, and may be stabilized by the phospholipids in the silicone base. By increasing the permeability of piroxicam, the time of treatment may be significantly reduced, and thus, reducing the time of results of treatment to a period of about 7 days.

According to various embodiments, the transdermal composition may be applied to an area of treatment for plantar fasciitis in a dose of about 0.5 g to about 2 g, once a day for about 7 days to about 60 days, depending on the severity of the condition. The area of treatment may be illustrated in FIG. 1 and FIG. 2.

Figure 2:
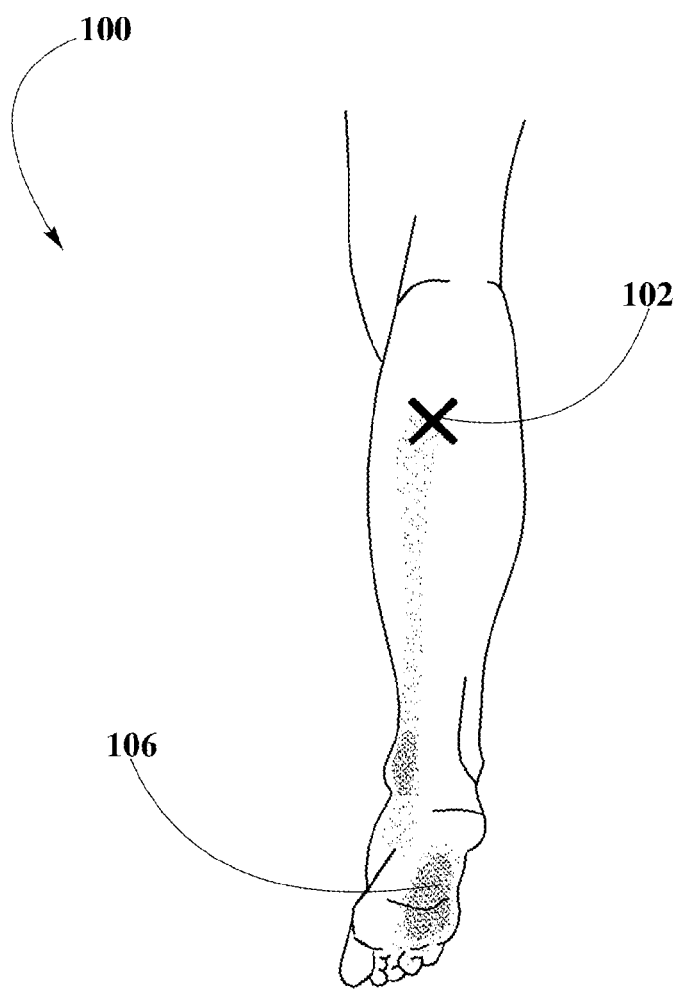
FIG. 2 depicts an area of treatment showing a myofascial trigger point of a bottom surface of a foot, where transdermal composition may be applied, according to an embodiment.

FIG. 1 and FIG. 2 illustrate area of treatment 100 where the transdermal composition may be applied. Area of treatment 100 may include myofascial trigger points 102. The transdermal composition may be smeared upon the calf, where myofascial trigger points 102 are located, to alleviate pain in heels 104 or bottom 106 of the foot. Pain caused by plantar fasciitis may be alleviated by the application of the transdermal composition upon the myofascial trigger points 102. Employing myofascial trigger points 102, the origin of the pain caused by plantar fasciitis may be treated more effectively. Moreover, employing a long acting NSAID such as piroxicam in combination with the NPE composition may act as a faster and effective treatment for an inflammatory process, such as plantar fasciitis, hence, only one dose every day may have to be applied in myofascial trigger points 102.

EXAMPLES

Example #1 is an embodiment of the transdermal composition, which, including a long-acting NSAID such as piroxicam, may be applied in a patient having a condition that needs a piroxicam treatment and, for any reason, If for any reason the patient may lack time for applying the transdermal composition multiple times in a day, the patient may apply the present transdermal composition only once a day, which may be enough for treating the condition.

Example #2 is an embodiment of transdermal composition, which may be applied in a patient having mild pain. The transdermal composition may be applied to the affected area in a dose of about 0.5 g to about 2 g, once a day for about 7 days to about 60 days.

What is claimed is:

1. A method for treating plantar fasciitis in a patient, comprising administering to the patient an effective amount of piroxicam, in a composition formulated for topical administration and comprising the piroxicam and at least one natural permeation enhancement composition.

2. The method, according to claim 1, wherein an effective amount of the piroxicam composition administered to the patient is about 5 to 200 mg per day.

3. The method according to claim 2, wherein the piroxicam composition is administered in multiple doses per day.

4. The method according to claim 1, wherein the composition comprises about 2% w/w of piroxicam.

5. The method according to claim 1, wherein the composition comprises about 95% w/w to about 98% w/w of at least one natural permeation enhancement composition.

6. The method according to claim 1, wherein the at least one natural permeation enhancement composition comprises one selected from the group comprising a phospholipid, an oil having essential fatty acids, at least one skin lipid, a butter having linoleic acid and linolenic acid, and combinations thereof.

7. The method according to claim 1, wherein the at least one natural permeation enhancement composition comprises about 0.05% w/w to about 5% w/w of one or more phospholipids.

8. The method according to claim 1, wherein the at least one natural permeation enhancement composition comprises about 1% w/w to about 20% w/w of at least one oil having essential fatty acids.

9. The method according to claim 8, wherein the essential fatty acids are selected from the group consisting of behenic acid, oleic acid, and combinations thereof.

10. The method according to claim 8, wherein the at least one oil is pracaxi oil.

11. The method according to claim 1, wherein the at least one natural permeation enhancement composition comprises about 0.1% w/w to about 3% w/w of at least one skin lipid.

12. The method according to claim 1, wherein the at least one natural permeation enhancement composition comprises about 1% w/w to about 10% w/w of at least one butter.

13. The method according to claim 12, wherein the at least one butter comprises one selected from the group consisting of linoleic acid, linolenic acid, and combinations thereof.

14. The method according to claim 1, wherein the at least one natural permeation enhancement composition comprises one selected from the group consisting of a hydrogenated phospholipid, an unsaturated phospholipid, pracaxi oil; *plukenetia volubilis* seed oil, ceramide, squalene, *vitellaria paradoxa* butter, and combinations thereof.

15. The method according to claim 1, wherein the at least one natural permeation enhancement composition comprises about 10% w/w to about 50% w/w of pracaxi oil.

16. The method according to claim 1, wherein the at least one natural permeation enhancement composition comprises about 15% w/w to about 40% w/w of patauá oil.

17. The method according to claim 1, wherein the at least one natural permeation enhancement composition comprises about 10% w/w to about 30% w/w of inaja oil.

18. The method according to claim 1, wherein the at least one natural permeation enhancement composition comprises about 10% w/w to about 30% w/w of at least one suitable emollient.

19. The method according to claim 1, wherein the at least one natural permeation enhancement composition comprises about 1% w/w to about 20% w/w of pracaxi oil, about 10% w/w to about 40% w/w of at least one phospholipid, about 5% w/w to about 20% w/w of an oil selected from the group consisting of seje oil, inaja oil, and combinations thereof, and about 5% w/w to about 30% w/w of at least one emulsifier.

\* \* \* \* \*